United States Patent
Levene et al.

(10) Patent No.: US 9,599,728 B2
(45) Date of Patent: Mar. 21, 2017

(54) SCINTILLATOR PACK COMPRISING AN X-RAY ABSORBING ENCAPSULATION AND X-RAY DETECTOR ARRAY COMPRISING SUCH SCINTILLATOR PACK

(71) Applicant: KONINKLIJKE PHILIPS N.V., Eindhoven (NL)

(72) Inventors: Simha Levene, D. N. Hanegev (IL); Nicolaas Johannes Anthonius Van Veen, Geldrop (NL); Lev Gregorian, Kibbutz Hamaapil (IL); Antonius Wilhelmus Maria De Laat, Den Dungen (NL); Gerardus Franciscus Cornelius Maria Lijten, Veldhoven (NL); Rafael Goshen, Haifa (IL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 34 days.

(21) Appl. No.: 14/358,058

(22) PCT Filed: Nov. 23, 2012

(86) PCT No.: PCT/IB2012/056665
§ 371 (c)(1),
(2) Date: May 14, 2014

(87) PCT Pub. No.: WO2013/080105
PCT Pub. Date: Jun. 6, 2013

(65) Prior Publication Data
US 2014/0321609 A1 Oct. 30, 2014

Related U.S. Application Data

(60) Provisional application No. 61/564,407, filed on Nov. 29, 2011.

(51) Int. Cl.
*G01T 1/208* (2006.01)
*G01T 1/20* (2006.01)
*G01N 23/04* (2006.01)

(52) U.S. Cl.
CPC ........... *G01T 1/208* (2013.01); *G01N 23/046* (2013.01); *G01T 1/2008* (2013.01); *G01T 1/2018* (2013.01)

(58) Field of Classification Search
CPC ..... G01T 1/208; G01T 1/2008; G01T 1/2018; G01N 23/046
(Continued)

(56) References Cited

U.S. PATENT DOCUMENTS 6,252,927 B1 * 6/2001 Wieczorek ............. A61B 6/032
250/367
6,495,845 B1 12/2002 Tsunota et al.
(Continued)

FOREIGN PATENT DOCUMENTS

CN 101115344 1/2008
CN 101142497 3/2008
(Continued)

*Primary Examiner* — David Porta
*Assistant Examiner* — Gisselle Gutierrez

(57) ABSTRACT

A scintillator pack (2) and a CT X-ray detector array (1) comprising such scintillator pack (2) are proposed. The scintillator pack (2) comprises an array of scintillator pixels (3). At a bottom surface (31) of each scintillator pixel (3), an X-ray absorbing encapsulation (13) is provided. This encapsulation (13) comprises an electrically insulating highly X-ray absorbing material having an atomic number greater than 60 such as, for example, Bismuth oxide ($Bi_2O_3$). The X-ray absorbing encapsulation (13) is interposed between the scintillator pixels (3) and an electronic circuit (19). The electronic circuit (19) may be provided as an ASIC in CMOS technology and may therefore be sensitive to X-ray induced
(Continued)

damage. The encapsulation (13) provides for good X-ray protection of such electronic circuit (19).

17 Claims, 1 Drawing Sheet

(58) Field of Classification Search
USPC ........................................ 250/370.09; 378/19
See application file for complete search history.

(56) References Cited

U.S. PATENT DOCUMENTS

| | | |
|---|---|---|
| 7,310,405 B2 | 12/2007 | Venkataramani et al. |
| 7,405,408 B2 | 7/2008 | Vogtmeier |
| 7,932,499 B2 | 4/2011 | Furuichi et al. |
| 7,968,853 B2 | 6/2011 | Altman et al. |
| 2002/0181647 A1* | 12/2002 | Venkataramani ....... G01T 1/202 378/19 |
| 2006/0027759 A1* | 2/2006 | Jiang ..................... G01T 1/2018 250/370.11 |
| 2006/0165214 A1* | 7/2006 | Mattson ............... G01N 23/046 378/19 |
| 2007/0221858 A1 | 9/2007 | Abenaim et al. |
| 2009/0121146 A1* | 5/2009 | Luhta .................... G01T 1/2018 250/370.11 |
| 2010/0200760 A1* | 8/2010 | Baeumer ............. H01L 27/1446 250/366 |
| 2010/0220833 A1 | 9/2010 | Levene et al. |
| 2011/0198503 A1 | 8/2011 | Koren |

FOREIGN PATENT DOCUMENTS

| | | |
|---|---|---|
| EP | 1298676 | 4/2003 |
| JP | 8122492 A | 5/1996 |
| JP | 2003028986 A | 1/2003 |
| JP | 2003084066 | 3/2003 |
| JP | 2005000573 | 1/2005 |
| JP | 2010096616 | 4/2010 |
| WO | 2004027454 A1 | 4/2004 |

* cited by examiner

SCINTILLATOR PACK COMPRISING AN X-RAY ABSORBING ENCAPSULATION AND X-RAY DETECTOR ARRAY COMPRISING SUCH SCINTILLATOR PACK

CROSS REFERENCE TO RELATED APPLICATIONS

This application is a national filing of PCT application Ser. No. PCT/IB2012/056665, filed Nov. 23, 2012, published as WO 2013/080105 A2 on Jun. 6, 2013, which claims the benefit of U.S. provisional application ser. no. 61/564,407 filed Nov. 29, 2011, which is incorporated herein by reference.

FIELD OF THE INVENTION

The present invention relates to a scintillator pack which may be used in an X-ray detector array for computer tomography (CT). Furthermore, the invention relates to an X-ray detector array comprising such scintillator pack.

BACKGROUND OF THE INVENTION

X-ray detector arrays may be used for various applications for detecting X-rays transmitted through a body, for example in medical imaging. A typical type of X-ray detector array used in CT scanners comprises a scintillator pack in which a multiplicity of scintillators is arranged as an array of scintillator pixels. The scintillators may be in the form of crystals, or ceramic scintillators, or composite scintillators. X-ray radiation entering one of the scintillator pixels generates scintillation radiation, for example, light in the visible spectral range. This light is detected using an array of associated photo detectors, arranged adjacent to the scintillator pixels. A photo detector may be associated with each of the scintillator pixels. When an x-ray photon is absorbed, the light is emitted omni-directionally by the scintillator, and all the surfaces of the scintillator element except that directed to the photo detector are therefore covered with a reflecting layer, which is generally a white powder incorporated in a resin, to direct that light into the photo detector. To reflect efficiently, this reflecting layer must be quite thick.

The array of photo detectors may be connected to an electronic circuit which serves, for example, for amplification, digitisation and/or multiplexing of electrical signals from the detector array.

Typically, not all of the x-rays incident upon the scintillator pack are absorbed. Residual X-radiation may be transmitted not only through the scintillator pixels themselves, but especially through the reflective layer in the inter-scintillator regions between them. This irradiation may be harmful to underlying electronic circuits.

A conventional scintillator is described in U.S. Pat. No. 7,310,405 B2. Therein, the reflective layer disposed in the inter-scintillator regions between the scintillator pixels comprises an X-ray absorbing material. The X-ray absorbing layer acts to absorb X-rays thereby protecting underlying regions of the inter-scintillator regions.

SUMMARY OF THE INVENTION

It may be seen as an object of the present invention to provide an alternative scintillator pack for use in an X-ray detector array, this scintillator pack allowing, inter alia, for simple manufacture and good X-ray protection for adjacent electronic circuitry.

Such object may be met by the scintillator pack and the X-ray detector array according to the independent claims. Advantageous embodiments are defined in the dependent claims.

According to a first aspect of the present invention, a scintillator pack is proposed, such scintillator pack comprising an array of scintillator pixels and an X-ray absorbing encapsulation. The scintillator pixels each have a top surface, a bottom surface and side surfaces. Therein, the scintillator pixels are arranged such that side surfaces of neighbouring scintillator pixels face each other. The X-ray absorbing encapsulation comprises an electrically insulating highly X-ray absorbing material. This highly X-ray absorbing material has an atomic number of more than 50, preferably more than 70, and more preferably more than 80. The X-ray absorbing encapsulation is arranged at the bottom surface of the scintillator pixels.

According to a second aspect of the present invention, an X-ray detector array is proposed. The X-ray detector array comprises the above-mentioned scintillator pack according to an embodiment of the first aspect of the invention and furthermore comprises an array of scintillation radiation detectors and an electronic circuit. Each of the scintillation radiation detectors is arranged adjacent to an associated scintillator pixel of the scintillator pack for detecting scintillation radiation generated in the scintillator pixel. The electronic circuit is electrically connected to the array of scintillation radiation detectors. The X-ray absorbing encapsulation of the scintillator pack is arranged between the array of scintillator pixels of the scintillator pack and the electronic circuit.

A gist of the present invention may be seen in the idea to provide a scintillator pack with a specific region which is adapted to be highly absorbing to irradiated X-rays. In an X-ray detector array, the X-rays typically impinge onto the scintillator pack at a top surface of the scintillator pixels. Part of the impinging X-rays is absorbed within the scintillator pixels. However, a substantial portion of the impinging X-rays may either be transmitted through the scintillator pixels or may go through the scintillator pack through gap regions between neighbouring scintillator pixels, such gap regions being typically provided for separating neighbouring scintillator pixels and including reflective material for reflecting optical radiation generated in each of the scintillator pixels towards an associated optical detector.

It is proposed to arrange an X-ray absorbing region, which is called herein "X-ray absorbing encapsulation", underneath the scintillator pixels, i. e. at the bottom surface of the scintillator pixels. The X-ray absorbing encapsulation comprises a material which is highly X-ray absorbing due to its material comprised therein having an atomic number, also referred to as "Z-Number", of more than 50.

As the X-ray absorbing encapsulation is arranged underneath the scintillator pixels, there is sufficient space available to provide the X-ray absorbing encapsulation with a sufficient thickness such that substantially no X-rays previously transmitted through the array of scintillator pixels is further transmitted through the X-ray absorbing encapsulation but are substantially completely absorbed in the encapsulation. The X-ray transmission of such layer may be e.g. approximately 3% at 50 KeV and 10% at 100 KeV. Accordingly, an electronic circuit arranged underneath the X-ray absorbing encapsulation is protected against damaging X-rays.

Due to the electrical insulation properties of the material for the X-ray absorbing encapsulation, electrical connections from the electronic circuit to the scintillator radiation detectors may be lead through the region of the encapsulation without requiring additional efforts for electrically separating such electrical connection for preventing e.g. short circuits.

The highly X-ray absorbing material comprised in the X-ray absorbing encapsulation may comprise Bismuth oxide ($Bi_2O_3$). Bismuth has an atomic number of 83 and is therefore highly X-ray absorbing. Furthermore, Bismuth oxide is non-poisonous, electrically insulating and may be provided at low cost.

The X-ray absorbing encapsulation may comprise between 20 and 70 vol-% (volume percent), preferably between 30 and 60 vol-%, and more preferably 50 +/− 5 vol-% of highly X-ray absorbing material such as Bismuth oxide. Such content of X-ray absorbing material has been shown to provide sufficient X-ray absorption. A remainder of the volume of the X-ray absorbing encapsulation may provide for other purposes. For example, material for forming the X-ray absorbing encapsulation may be provided with a resin thereby, in an uncured viscous state, enabling a sufficiently low viscosity to enable its application as an encapsulation.

For example, the X-ray absorbing encapsulation may comprise particles of the highly X-ray absorbing material such as the Bismuth oxide, the particles being included in a matrix material. The particles may provide for the required X-ray absorption due to the heavy elements comprises therein. The matrix material may enclose the particles and provide for structural stability of the highly X-ray absorbing material. The matrix material may be a curable material which, in an initial state, is fluid and which may then cure to come into a stable solid state. Both the particles and the matrix material may be electrically insulating.

A majority of the particles, for example, at least 90%, preferable at least 95% of the particles may have a size of between 1 and 50 micrometers, preferably between 3 and 20 micrometers. Such size distribution has been shown to have advantageous properties for example with respect to e.g. rheological characteristics of a non-cured particle/matrix-material mixture during filling of empty spaces for generating the X-ray absorbing encapsulation while having adequate X-ray absorbing characteristics.

The particles may be incorporated into a matrix material comprising, for example, epoxy resin. Epoxy resin is electrically insulating, and may have a sufficiently low viscosity before curing, is easy to handle and may be provided at low cost.

Accordingly, a material used for filling the volume of the X-ray absorbing encapsulation may be prepared by mixing a powder of particles of the highly X-ray absorbing material into the matrix material which, at an initial stage, is liquid and may subsequently be cured. For example, Bismuth oxide particles may be mixed into epoxy resin and the mixture then filled into the volume of the X-ray absorbing encapsulation and subsequently cured. An additive such as a disperant may be added to the mixture to assist dispersion of the powder particles in the epoxy. Accordingly, such X-ray absorbing encapsulation for a scintillator pack may be easily manufactured and may be provided at low cost.

For example, the X-ray absorbing encapsulation may cover at least 80%, more preferably at least 95% of the bottom surface of each of scintillator pixels comprised in the scintillator pack. Accordingly, in an area of the scintillator pack where, for example, an underlying electronic circuit has to be protected against X-ray damaging, at least the major portion of the bottom surface of the scintillator pixels is covered by a sufficiently thick layer of the X-ray absorbing encapsulation. Preferably, the entire area to be protected against X-ray damaging is covered by the X-ray absorbing encapsulation either alone or in combination with other X-ray absorbing means such that the electronic circuit is completely protected against X-ray damaging.

Separating spaces between neighbouring scintillator pixels may be at least partially filled with a material which is at most weakly X-ray absorbing. In other words, while any material shows a specific X-ray absorption, the material provided in spaces separating neighbouring scintillator pixels may have a substantially weaker X-ray absorption than the material used for the X-ray absorbing encapsulation. For example, the separating spaces between neighbouring scintillator pixels may be provided with a material such as titanium dioxide ($TiO_2$) showing higher reflection to light generated by the x-rays absorbed in the scintillator pixels, but providing only poor X-ray absorption. However, in the proposed scintillator pack, such poor X-ray absorption in spaces between neighbouring scintillator pixels do not result in the transmission of X-ray radiation to underlying electronic circuitry, as the additional X-ray absorbing encapsulation arranged underneath such separating spaces will absorb such X-rays due to the highly X-ray absorbing material comprised therein. In contrast to the material provided in spaces separating neighbouring scintillator pixels, the highly X-ray absorbing material comprised in the encapsulation need not be highly reflective for light. Accordingly, different materials may be used for the X-ray absorbing encapsulation, on the one hand, and for the reflective layer in the separating spaces, on the other hand, such that no compromises or trade-offs have to be made with respect to X-ray absorption and light reflection, respectively.

The proposed scintillator pack may be specifically beneficial in an X-ray detector array when the electronic circuit of the X-ray detector comprises an integrated circuitry provided in CMOS technology. While an electronic chip comprising CMOS circuitry may be produced at low cost and at high integration, the CMOS structures may be sensitive to X-ray damage. However, due to the X-ray absorbing encapsulation comprised in the proposed scintillator pack, such CMOS circuitry is well-protected against X-ray irradiation.

Advantageously, the electronic circuit may comprise a flip chip ASIC (application specific integrated circuit). An ASIC may be produced at low cost using, for example, CMOS technology and may then be connected to a substrate and/or to the array of scintillation radiation detectors using flip chip technology. Due to the fact that the highly X-ray absorbing encapsulation may be provided with a curable resin as a matrix material, electrical connections between the ASIC and each of the scintillation radiation detectors may be easily led through the encapsulation, as the electrical connection may be prepared first and the encapsulation may be prepared by introducing the curable X-ray absorbing material subsequently into the spaces between such electrical connections.

According to an embodiment of the proposed X-ray detector array, a scintillation radiation detection surface of each one of the scintillation radiation detectors is arranged along a side surface of an associated scintillator pixel. In other words, for each pixel of the scintillator pack, an associated photo-detector may be provided and a detecting surface thereof may be arranged not at a bottom side but at a side surface of the associated scintillator pixel. However, those skilled in the art will recognise that the use of X-ray absorbing encapsulation material or under-fill may be advantageous in other detector array geometries wherein the photo-detecting surface is situated at a bottom side, not at a side surface of its associated scintillator pixel.

Accordingly, X-ray radiation may enter the scintillator pixel at a top surface and may generate scintillation radiation which may then be detected by the radiation detection surface at the side of the scintillator pixel whereas non-absorbed X-rays transmitted through the scintillator pixel will be subsequently absorbed in the underlying X-ray absorbing encapsulation, thereby preventing any X-ray damaging of underlying electronic circuitry.

The X-ray detector array may further comprise an interposer interposed between the X-ray absorbing encapsulation of the scintillator pack and the electronic circuit. The purpose of such interposer may be to provide a mechanically stable network of electrical interconnects between vertical optical detectors and front-end electronics, which are situated at the underside of the interposer, It is to be noted that possible features and advantages of embodiments of the present invention are described herein partly with respect to a proposed scintillator pack and partly with respect to a proposed X-ray detector array. A person skilled in the art will realize that the described features may be exchanged or combined in various ways thereby coming to alternative embodiments of the present invention and possibly thereby realizing synergy effects.

BRIEF DESCRIPTION OF THE DRAWINGS

Embodiments of the present invention will be described in the following with respect to the attached drawings wherein neither the description nor the drawings shall be interpreted as limiting the scope of the invention.

The figures are only schematically and not to scale.

DETAILED DESCRIPTION OF EMBODIMENTS

Figure 1:
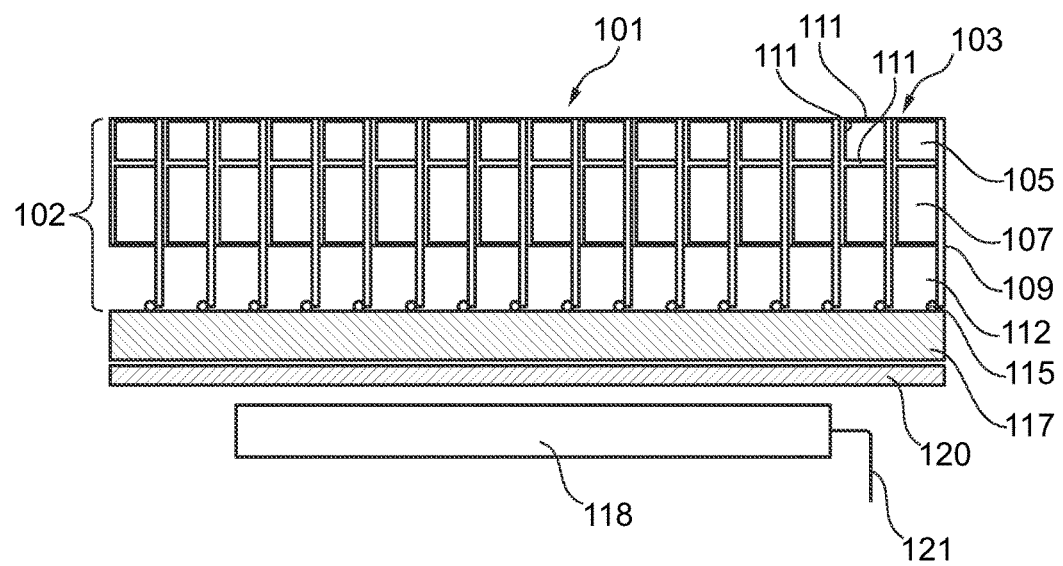
FIG. 1 shows an example of a conventional X-ray detector array.

An X-ray detector array such as shown in FIG. 1 has been provided e. g. for computer tomography.

The X-ray detector array 101 comprises a scintillator pack 102. In this scintillator pack 102, a plurality of scintillator pixels 103 is arranged in an array. Each scintillator pixel 103 comprises scintillator crystals 105, 107 which may convert penetrating X-rays into scintillation radiation, possibly in the visible spectral range. There are two layers of scintillators, the upper layer, i.e. nearer the x-ray source, to capture only the softer x-rays, and the lower layer, i.e. more distal from the x-ray source, to capture the harder x-rays. Each of the scintillators in each layer is associated with a photodiode. A spectral x-ray image is constructed by processing and comparing the data output from these two photodiode array layers. A more extensive description of this scintillator arrangement is given in U.S. Pat. No. 7,968,853 B2 and US 2010/0220833 co-owned by the assignee of the present application.

A scintillation radiation detector 109 is arranged adjacent to each of the scintillator pixels 103 at a side surface thereof. The scintillation radiation detector 109 may be provided as a vertical photodiode. Except for the side surface which is facing the scintillation radiation detector 109, all surfaces of the scintillator crystals are covered by a layer 111 of reflective paint which is highly reflective to scintillation radiation and which may reflect the scintillation radiation generated in the scintillator crystals towards an associated scintillation radiation detector surface. Each of the scintillator radiation detectors 109 is connected to a substrate 117 with an electrical joint 115 at a lower edge thereof. At a surface of the substrate 117 opposite to the surface directed to the scintillator pack 102, electronic circuits 118 are arranged. Furthermore, an optionally flexible input/output cable 121 is provided for electrically contacting the electronic circuit 118.

The electronic circuit 118 may serve for amplification, digitization and/or multiplexing and is arranged below the substrate 117. As the electronic circuit 118 may comprise an analog section dedicated, for example, to the amplification of fast changing currents in the pico-ampere range, it may be specifically this section which needs to be protected from direct X-ray radiation as such X-ray radiation may give rise to direct conversion and thereby to spurious signals. Furthermore, extended exposure may lead to damage, for example in the semiconductor material used for an integrated circuitry implementing the analog section and may thereby enhance leakage currents.

In order to protect the electronic circuit 118 and specifically protect its analog section, a plate 120 made of tungsten or any other suitable material of high atomic number Z is placed between the substrate 117 and the electronic circuit 118. In this approach, the electronic circuit 118 is mounted with its backside on the plate 120 and interconnections may be realized through wire bonding.

However, in such approach, all signals may have to be routed to a periphery of the electronic circuit 118. In a detector array with a large number of pixels 103, it may not be possible to route all signals to the periphery of the array.

Therefore, it may be advantageous to mount a chip implementing the electronic circuit 113 using flip chip technology. Thus, signal routing can be shorter and also power distribution over the chip can be controlled in a better way. However, in such approach, a new solution for protecting the electronic circuit 118 is to be sought.

Therefore, while in the X-ray detector array 101 of FIG. 1 a space 112 underneath the scintillators 105, 107 is empty; it is proposed to use this space for additional X-ray protection.

Figure 2:
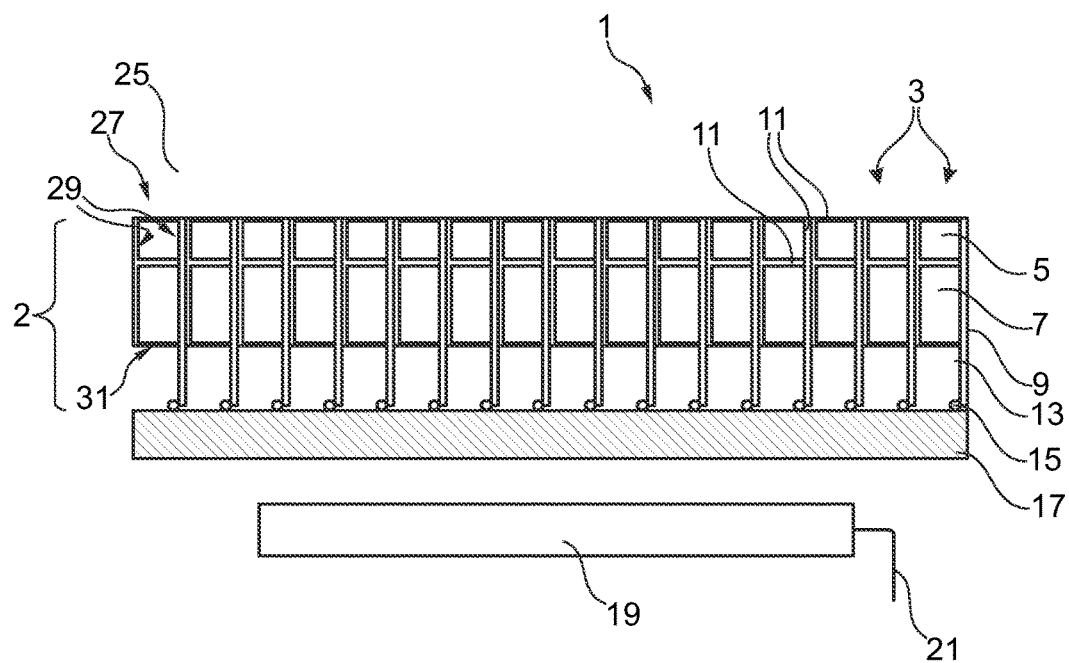
FIG. 2 shows an embodiment of an X-ray detector array according to the present invention.

FIG. 2 shows an embodiment of an X-ray detector array 1 according to the present invention.

A scintillator pack 2 comprises a plurality of scintillator pixels 3 each comprising scintillators 5, 7. Each of the scintillators 5, 7 is enclosed by a layer 11 of reflective paint in order to reflect scintillation radiation generated within the respective scintillator pixel 3 towards a side surface thereof. At this side surface, a vertical photo diode serves as a scintillation radiation detector 9. Each scintillation radiation detector 9 is connected via an electrical joint 15 to an interposer 17. At an opposite side of the interposer 17, ASICs are arranged for providing an electronic circuit 19. The ASICs are mounted in flip chip technology and are connected to an input/output cable 21.

In X-ray applications, a top surface 27 of the scintillator pixels 3 is directed towards an X-ray source. X-rays may enter the scintillators 5, 7 and may be at least partly absorbed to generate scintillation radiation therein. Side surfaces 29 of the scintillator pixels 3 are covered with the layer 11 of reflective paint or by an associated scintillation radiation detector 9.

At a bottom surface 31 of the scintillator pixels 3, a volume between the scintillator crystals 7 and the interposer 17 is filled with a highly X-ray absorbing material thereby forming an X-ray absorbing encapsulation 13. This X-ray absorbing encapsulation 13 comprises a high volume percentage of highly X-ray absorbing material having a high atomic number of more than 50. Due to this highly X-ray absorbing material, the encapsulation 13 may serve as an X-ray protection barrier for the underlying electronic circuit 19. Substantially no X-rays transmitted through the scintillator pixels 3 may be further transmitted through the encapsulation 13 due to its highly X-ray absorbing characteristics.

The encapsulation 13 may not only act as an X-ray barrier but may also serve for mechanical stabilization of the photodiodes forming the scintillation radiation detectors 9 on top of the interposer 17.

A filler material used for the encapsulation 13 may be, for example, Bismuth oxide ($Bi_2O_3$). The high atomic number of Bismuth provides for good X-ray absorption properties of such filler material. It has been observed that an X-ray absorbing encapsulation 13 comprising e.g. a high content of Bismuth oxide and having a thickness of 1 mm may show similar X-ray absorption properties as a Tungsten plate of 0.25 mm. Furthermore Bismuth oxide is environmentally acceptable, non-poisonous and is a low cost material.

As the Bismuth is provided in an oxidized form, the filler material is sufficiently electrically insulating such that e. g. spurious electrical shorts between the electrical joints 15 may be prevented. As the photodiodes of the scintillation radiation detectors 9 may provide photo currents in the range of pico-ampere, such electrical insulation may be crucial. An electrical resistance of more than hundred Mega-Ohm (>100 MΩ) between neighbouring electrical joints may have to be achieved.

As an alternative to Bismuth oxide as a filler material, other filler materials including high Z number elements such as Lead oxide ($Pb_xO_y$), Tantalum oxide ($Ta_2O_5$), Uranium oxide ($UO_2$), Lutetium oxide ($Lu_2O_3$), Gadolinium oxide ($Gd_2O_3$) or other suitable oxides may be used. As a further alternative, Tungsten metal particles coated with an isolating layer to maintain electrical insulation may be used in the X-ray absorbing encapsulation 13.

The filler material may, but does not necessarily have to, provide for high reflectivity to scintillation radiation. For example, Bismuth oxide shows some absorption in the visible spectrum and has a yellowish appearance. However, in the X-ray detector array proposed herein, such absorption does not matter as the filling material in the encapsulation 13 does not have to serve for reflecting scintillation radiation as this effect is obtained by the layer 11 of reflective paint.

The filler material for the encapsulation 13 may include particles of highly X-ray absorbing material such as Bismuth oxide, such particles being integrated into a resin matrix. A filling degree is preferably as high as possible, but for practical reasons may be about 50% by volume or 90% by weight. At such formulation, a viscosity may still be low enough such that the particle resin mixture can be used for a filling process for filling spaces underneath the scintillator pixels 3 in order to generate the X-ray absorbing encapsulation 13.

For example, a powder comprising Bismuth oxide particles of an average size of 10 micrometers may be mixed with low-viscous epoxy adhesives. In order to obtain the low-viscous, highly loaded Bismuth oxide filler, an effective dispersant is required to disperse the Bismuth oxide particles in the filler material. Maximum particle content may further be influenced by particle properties such as size, size distribution and shape. The properties of the filler material, particularly its viscosity and its content of Bismuth oxide particles, may be adapted such that, on the one hand, the filler material may be easily introduced into the spaces underneath the scintillator pixels 3 in order to generate the X-ray absorbing encapsulation 13 and, on the other hand, provide for sufficient X-ray absorption by such encapsulation 13. While a high content of X-ray absorbing particles, i. e. Bismuth oxide particles, provides for high X-ray absorption, such high content may result in high viscosity. Accordingly, the content of X-ray absorbing particles within the resin matrix of the filler material will have to be optimized.

It should be noted that the term "comprising" does not exclude other elements or steps and that the indefinite article "a" or "an" does not exclude the plural. Also elements described in association with different embodiments may be combined. It should also be noted that reference signs in the claims shall not be construed as limiting the scope of the claims.

LIST OF REFERENCE SIGNS

1 X-ray detector array
2 scintillator pack
3 scintillator pixel
5 scintillator
7 scintillator
9 scintillation radiation detector
11 layer of reflective paint
13 X-ray absorbing encapsulation
15 electrical joint
17 interposer
19 electronic circuit
21 input/output cable
27 top surface
29 side surface
31 bottom surface
101 detector array
102 scintillator pack
103 scintillator pixel
105 scintillator
107 scintillator
109 scintillation radiation detector
111 layer of reflective paint
112 empty space
115 electrical joint
117 plate
118 electronic circuit
121 input/output cable

The invention claimed is:

1. An X-ray detector array comprising:
an array of scintillator pixels, wherein a scintillator pixel includes a top surface, a bottom surface, and at least two scintillators with a plurality of surfaces covered in a layer of reflective paint and stacked one on top of the other;
an interposer having a first side and a second side, which is a side opposite the first side;
a plurality of vertical radiation detectors, wherein a vertical scintillation radiation detector is at a side surface of the scintillator pixel contacting the at least two scintillators, includes a sub-portion with an end that extends beyond the bottom surface of the scintillator pixel, and the end is connected via an electrical joint to the first side of the interposer;
wherein the bottom surface of the scintillator pixel is separated from the interposer by a non-zero distance with a non-zero volume directly there between; and
an X-ray absorbing encapsulation material comprising an electrically insulating highly X-ray absorbing material, wherein the highly X-ray absorbing material has an atomic number greater than 50, and the X-ray absorbing encapsulation material is disposed in the volume between and contiguous to one of the covered surfaces of one of the at least two scintillators and the interposer, and next to the sub-portion.

2. The X-ray detector array of claim 1, wherein the highly X-ray absorbing material comprises Bismuth oxide.

3. The X-ray detector array of claim 1, wherein the X-ray absorbing encapsulation material comprises between 20 and 70 vol-% of the highly X-ray absorbing material.

4. The X-ray detector array of claim 1, wherein the X-ray absorbing encapsulation material comprises particles of the highly X-ray absorbing material, the particles being included in a matrix material of epoxy resin.

5. The X-ray detector array of claim 4, wherein 90% of the particles have a size of between 1 and 50 µm.

6. The X-ray detector array of claim 1, further including a reflective material enclosing the scintillator pixel except on the side contacting the vertical scintillation radiation detector.

7. The X-ray detector array of claim 1, wherein the X-ray absorbing encapsulation material covers at least 80% of the bottom surface of the scintillator pixel.

8. The X-ray detector array of claim 1, wherein separating spaces between neighboring scintillator pixels are at least partially filled with a weakly X-ray absorbing material.

9. The X-ray detector array of claim 1, wherein the X-ray absorbing material comprises a mixture of materials having different atomic numbers that includes at least one of Lead oxide ($Pb_xO_y$), Tantalum oxide ($Ta_2O_5$), Uranium oxide ($UO_2$), Lutetium oxide ($Lu_2O_3$) or Gadolinium oxide ($Gd_2O_3$).

10. The X-ray detector array of claim 1, further comprising:
an electronic circuit electrically connected on the second side of the interposer.

11. The X-ray detector array of claim 10, wherein the electronic circuit comprises an integrated circuitry provided in CMOS technology.

12. The X-ray detector array of claim 10, wherein the electronic circuit comprises a flip chip ASIC.

13. The X-ray detector array of claim 10, further comprising:
an interposer interposed between the X-ray absorbing encapsulation material and the electronic circuit.

14. A CT scanner comprising an X-ray detector array according to claim 1, further comprising:
an x-ray radiation source; and
wherein the top surface of the scintillator pixels is directed towards the x-ray radiation source.

15. The X-ray detector array of claim 1, wherein the scintillation radiation detectors is configured to detect the scintillation radiation generated by the scintillator pixel.

16. The X-ray detector array of claim 1, wherein the X-ray absorbing encapsulation material provides structural stability of the electrically insulating highly X-ray absorbing material.

17. The X-ray detector array of claim 4, wherein the X-ray absorbing encapsulation material includes a dispersant that assists dispersion of the particles in the matrix material.

* * * * *